United States Patent [19]

Lekholm et al.

[11] Patent Number: 4,697,591
[45] Date of Patent: Oct. 6, 1987

[54] CARDIAC PACER FOR PACING A HUMAN HEART AND PACING METHOD

[75] Inventors: Anders Lekholm; David C. Amundson, both of Bromma, Sweden

[73] Assignee: Siemens Aktiengesellschaft, Berlin and Munich

[21] Appl. No.: 874,591

[22] Filed: Jun. 16, 1986

[51] Int. Cl.$^4$ .............................................. A61N 1/36
[52] U.S. Cl. .............................. 128/419 PG; 128/716
[58] Field of Search ........................ 128/419 PG, 716

[56] References Cited

U.S. PATENT DOCUMENTS

| 3,593,718 | 7/1971 | Krusner et al. | 128/419 P |
| 4,303,075 | 12/1981 | Heilman et al. | 128/419 PG |
| 4,428,378 | 1/1984 | Anderson et al. | 128/419 PG |
| 4,567,892 | 2/1986 | Plicchi et al. | 128/419 PG |

FOREIGN PATENT DOCUMENTS 0089014  10/1983  European Pat. Off. .

Primary Examiner—William E. Kamm
Assistant Examiner—Timothy J. Keegan
Attorney, Agent, or Firm—Hill, Van Santen, Steadman & Simpson

[57] ABSTRACT

A cardiac pacer which generates pacing pulses at a predetermined pacing rate includes a device for processing the pacing pulses according to an impedance measurement such that a respiratory signal is obtained. The predetermined pacing rate is then varied dependent on the respiratory signal.

15 Claims, 2 Drawing Figures

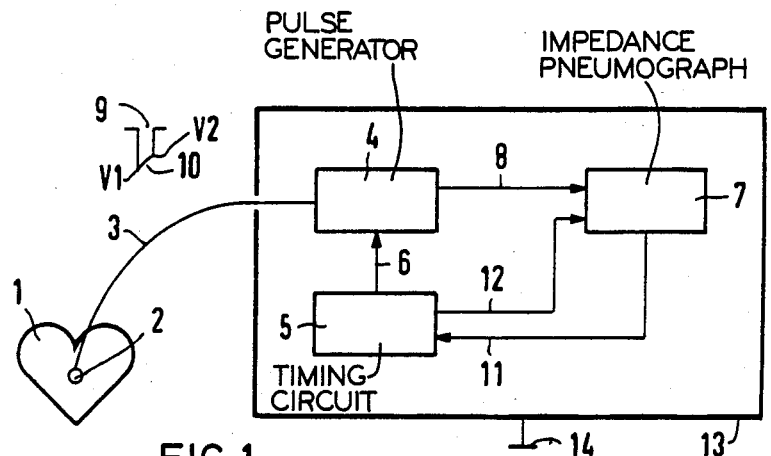
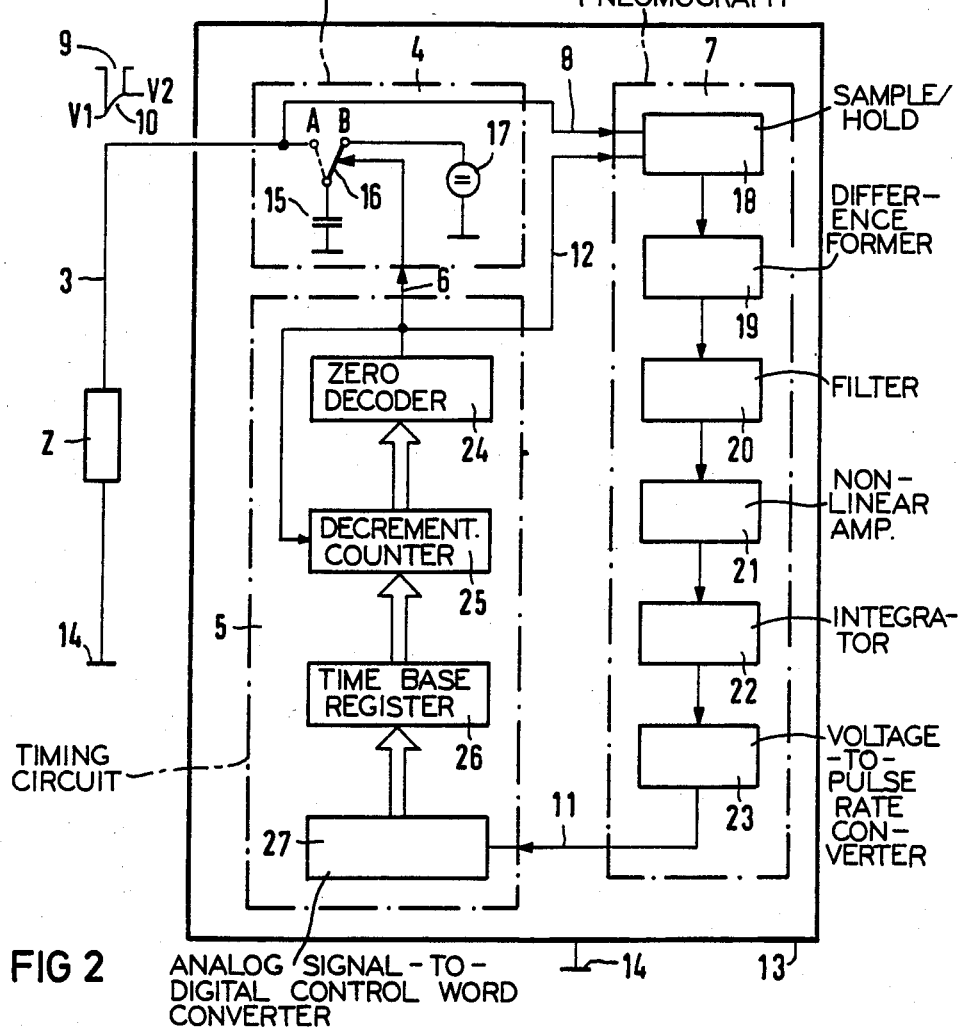

CARDIAC PACER FOR PACING A HUMAN HEART AND PACING METHOD

BACKGROUND OF THE INVENTION

1. Field of the Invention

This invention relates to a cardiac pacer for pacing a human heart, wherein the pacing rate is controlled by the respiration of the patient.

2. Related Applications:

The subject matter of the present application is related to the subject matter of the following co-pending applications filed simultaneously herewith: "A Cardiac Pacer For Pacing A Human Heart," Amundson, Ser. No. 874,588; "A Cardiac Pacer For Pacing A Heart," Elmqvist, Lekholm, Hedberg and Amundson, Ser. No. 874,597; "A Cardiac Pacer For Pacing A Heart," Lekholm and Amundson, Ser. No. 874,596; and "A Cardiac Pacer For Pacing A Heart," Lekholm and Amundson, Ser. No. 874,585.

3. Description of the Prior Art

Conventional cardiac pacers usually comprise a pacing electrode and a passive electrode. The pacing electrode is placed in the human heart by means of a pacing lead. The conductive (metallic) housing of the cardiac pacer defines the passive electrode.

The U.S. Pat. No. 3,593,718 describes such a conventional cardiac pacer which in addition utilizes an impedance pneumograph for obtaining a respiratory signal from thoracic impedance variations. The impedance pneumograph comprises a first and a second impedance measuring electrodes each connected with a separate first and second leads, respectively. Both impedance measuring electrodes of the impedance pneumograph are placed on the surface of the patient's chest.

The European Patent Application No. 0 089 014 depicts a conventional cardiac pacer which also employs an impedance pneumograph for obtaining a respiratory signal. Again the impedance pneumograh comprises first and a second impedance measuring electrodes. However, only the first impedance measuring electrode is connected to a lead while the second electrode is defined by the conductive (metallic) housing which contains the cardiac pacer and the impedance pneumograph. Furthermore, the first impedance measuring electrode and, since the conductive (metallic) housing is implanted, the second electrode are subcutaneously placed in the thorax. Under the circumstances the complete pacing and impedance measuring system comprises a pacing electrode on a first lead, a first impedance measuring electrode on a second lead and the metallic housing as both the passive electrode of the cardiac pacer and the second electrode of the impedance pneumograph. Finally the current impulses generated and utilized for impedance measurement are at a higher rate than those of the ventilation rate. Under the circumstances the pacer needs an unnecessary high amount of energy.

SUMMARY OF THE INVENTION

Objects

It is an object of this invention to provide for an improved cardiac pacer for pacing a human heart wherein the pacing rate is controlled by the respiration rate of the patient, and wherein the number of necessary electrodes and therefore also the number of necessary leads for obtaining a respiratory signal from thoracic impedance variations is reduced to a minimum. Furthermore the amount of energy necessary to activate the respiration rate measuring means should be reduced to a minimum.

Summary

According to this invention an improved cardiac pacer is provided which comprises (a) means for generating pacing pulses at a predetermined pacing rate;

(b) means for transmitting the pacing pulses to the human heart for pacing;

(c) means for processing the pacing pulses for obtaining respiratory signal according to an impedance measurement; and (d) means for varying the predetermined pacing rate dependent on the respiratory signal.

By utilizing the pacing pulses for obtaining a respiratory signal the amount of energy to activate the respiration measuring means is reduced to a minimum. Furthermore it is possible to operate with only two electrodes and one lead for both pacing and measuring the impedance variations, namely the pacing electrode connected to the pacing lead and the metallic housing containing the pacer and the impedance pneumograph. Under the circumstances the invention provides for a minimum number of electrodes and leads for pacing and impedance measurement. Since the pacing pulse itself is processed for obtaining a respiratory signal no additional current for impedance measurement has to be supplied.

The foregoing and other objects, features and advantages of the invention will be apparent from the following more particular description of a preferred embodiment of the invention, as illustrated in the accompanying drawings.

BRIEF DESCRIPTION OF THE DRAWINGS

FIG. 1 shows the invention in a schematic block diagram; and

FIG. 2 illustrates the invention in a more detailed block diagram.

DESCRIPTION OF THE PREFERRED EMBODIMENT

In FIG. 1 a human heart which has to be paced is generally designated with 1. A pacing electrode 2 is inserted in the human heart 1 in a manner and position that the heart can most efficiently be paced. The pacing electrode 2 is connected through a pacing lead 3 with a pacing pulse generator 4. A timing circuit 5 controls the pacing rate of the pacing pulse generator 4 through line 6. An impedance pneumograph 7 is connected with the pacing pulse generator 4 through line 8 for processing the pacing pulses 9 in a manner that a respiratory signal is obtained from the pacing pulses 9 when evaluating the amplitude decays 10 of pacing pulses 9. The amplitude decay 10 changes according to alternating body impedance during respiration.

Alternatively, the impedance measurement can be done by the simultaneous measurement of voltage and its associated current and an analog or digital division of voltage and current.

The impedance pneumograph 7 controls the timing circuit 5 through line 11 such that a predetermined basic pacing rate of the pacing pulse generator 4 is varied dependent on the respiratory signal. The line 12 is a control line from the time base unit 5 to the impedance pneumograph 7.

In FIG. 1 the pacing pulse generator 4, the timing circuit 5 and the impedance penumograph 7 are all encapsuled in an implantable conductive (metallic) housing 13 which is the housing of the cardiac pacer according this invention. The metallic housing 13 defines both the passive electrode for pacing and the second electrode for impedance measurement as indicated in FIG. 1 with reference numeral 14. Under the circumstances the cardiac pacer according to this invention operates with only two electrodes and one lead, namely electrodes 2 and 14 and lead 3 for both pacing and impedance measurement. Since the pacing pulse itself is processed for obtaining a respiratory signal no additional current for impedance measurement has to be supplied. Therefore the amount of energy necessary for activating impedance measurement is reduced to a minimum.

FIG. 2 depicts the schematic block diagram of FIG. 1 in more detail. The complete impedance including the heart is designated with Z. The pacing pulse generator 4 comprises an output capacitor 15 which is switchable by means of switch 16 between battery 17 (switch position B) and pacing lead 3 (switch position A). In switch position B the output capacitor 15 is charged by the battery 17 to a voltage V1. In switch position A the output capacitor 15 is discharged through pacing lead 3 as pacing pulse 9. The amount of discharge depends on the impedance variations of the patient's thorax during respiration. According to FIG. 2 the pacing pulse 9 discharges from V1 to V2 (amplitude decay 10).

The impedance pneumograph 7 includes sample and hold circuitry 18, a difference former 19, a filter 20, non-linear amplification (e.g. squaring) circuitry 21, an integrator 22 and a voltage to pulse rate converter 23. The sample and hold circuitry 18 samples and holds the voltages V1, V2 of output capacitor 15. The difference former 19 supplies the difference V1-V2 through the filter 20 to the non-linear amplification circuitry 21. The non-linear amplification circuitry 21 amplifies the output signal of filter 20 such that signal portions having higher amplitudes are more amplified than signal portions having lower amplitudes. Under the circumstances signal portions of interest, including the respiration signal, are enhanced with respect to low amplitude noise for further processing. Non-linear amplification circuitries of this kind are well known in the art and need not be described in more detail. The output signal of the non-linear amplification circuitry 21 is integrated in integrator 22 over a period of time, e.g. in the range of 5 to 30 s. By integrating, high-frequency noise is significantly reduced. The voltage to pulse rate converter converts the integrated signal into a pulse rate according to the breathing rate.

The timing circuit 5 comprises a zero decoder 24, a decremental counter 25, a time base register 26 and an analog signal to digital control word converter 27. The converter 27 converts the analog pulse rate signal of the voltage to pulse rate converter 23 into a digital control word. This digital control word is supplied to the time base register 26. It controls the time base register 26 such that a basic pacing rate, e.g. 60 beat/min., is varied dependent on the respiration rate. When the breathing rate increases the time base register 26 increases the counting speed of down counter 25 so that it reaches zero faster than at basic rate. Under these conditions the zero decoder 24 generates switching signals at higher rates, so that the output capacitor 15 of the pacing pulse generator 4 charges and discharges at higher rates. As a result the pacing rate increases dependent on increasing breathing rate as desired.

Having thus described the invention with particular reference to the preferred forms thereof, it will be obvious to those skilled in the art to which the invention pertains, after understanding the invention, that various changes and modifications may be made therein without departing from the spirit and scope of the invention as defined by the claims apended hereto.

What is claimed is:

1. A cardiac pacer for pacing a human heart in a patient comprising
    (a) means for generating pacing pulses at a predetermined pacing rate;
    (b) means for transmitting the pacing pulses to the human heart for pacing;
    (c) means for processing the pacing pulses for obtaining a respiratory signal according to a monitored impedance change in said patient; and
    (d) means for varying the predetermined pacing rate dependent on the respiratory signal.

2. A cardiac pacer as claimed in claim 1, further comprising
    (a) means for non-linearly amplifying the respiratory signal such that signal portions having higher amplitudes are more amplified than signal portions having lower amplitudes;
    (b) means for integrating the non-linearly amplified respiratory signal over a period of time; and
    (c) wherein said means for varying the predetermined pacing rate varies the pacing rate dependent on the integrated signal.

3. A cardiac pacer as claimed in claim 1, wherein said means for processing includes means for measuring the amplitude of a pacing pulses at the beginning and the amplitude of the same pacing pulse at the end of the pacing pulse and means for obtaining a measure for the decay between the two amplitudes which is a measure for the respiration.

4. A cardiac pacer as claimed in claim 3, wherein said means for measuring the amplitudes comprises a sample and hold circuitry.

5. A cardiac pacer as claimed in claim 3, wherein said means for obtaining measure for the decay comprises a difference former for the amplitudes.

6. A cardiac pacer as claimed in claim 2, wherein said means for processing the pacing pulses further comprises a voltage to pulse rate converter for the integrated signal.

7. A cardiac pacer as claimed in claim 6, wherein said means for varying the predetermined pacing rate comprises an analog signal to digital control word converter for the output signal of the voltage to pulse rate converter, a time register of the output signal of the analog signal to digital control word converter, a decremental counter which is set to higher zero counting speed when the respiration rate increases and a zero decoder at the output of the down counter, said zero decoder being connected with and controlling the pacing pulse generator such that a pacing pulse is generated at each zero count.

8. A method for pacing a human heart in a patient comprising the steps of:
    generating pacing pulses at a selected pacing rate;
    transmitting the pacing pulses to the heart for pacing thereof;

measuring said pacing pulses after transmittal to said heart for obtaining a respiratory signal therefrom corresponding to respiratory activity of said patient; and varying said selected pacing rate in dependence on said respiratory signal.

9. A method as claimed in claim 8, wherein the step of measuring said pacing pulses is further defined by monitoring an impedance change of said pacing pulses.

10. A method as claimed in claim 9, wherein the step of taking an impedance measurement of said pacing pulses is further defined by the steps of:

measuring the amplitude of a pacing pulse at the beginning thereof;

measuring the amplitude of the same pacing pulse at the end thereof; and measuring any decay existing between the two amplitude measurements.

11. A method as claimed in claim 10 wherein the steps of measuring the amplitudes of the beginning and the end of said pacing pulse is undertaken using sample and hold circuitry.

12. A method as claimed in claim 10, wherein the step of measuring said decay is further defined by forming the difference between the beginning amplitude and the end amplitude of said pacing pulse.

13. A method as claimed in claim 8, comprising the additional steps of:

non-linearly amplifying said respiratory signal for more greately amplifying portions of said respiratory signal having higher amplitudes than signal portions having lower amplitudes;

integrating the non-linearly amplified respiratory signal over a selected period of time; and wherein the step of varying the predetermined pacing rate is further defined by varying the pacing rate dependent on the integrated signal.

14. A method as claimed in claim 13 comprising the additional step of:

converting said integrated signal into a pulse rate signal for use in varying said predetermined pacing rate.

15. A method as claimed in claim 14, comprising the additional steps of:

converting said pulse rate into a digital control word;

supplying said digital control word to a time base register for selecting a time base therein corresponding to said digital control word;

using said time base to decrement a counter, said counter counting down at a higher speed as respiratory acitivty of said patient increases; and generating a pacing pulse each time said counter reaches zero, and simultaneously resetting said counter.

* * * * *